United States Patent [19]

Boron

[11] 4,007,640
[45] Feb. 15, 1977

[54] SAMPLING APPARATUS

[75] Inventor: Joseph J. Boron, Medina, Ohio

[73] Assignee: Aikoh Co., Ltd., Tokyo, Japan

[22] Filed: Jan. 23, 1976

[21] Appl. No.: 651,710

[52] U.S. Cl. .................... 73/425.4 R; 73/DIG. 9
[51] Int. Cl.$^2$ .................................... G01N 1/20
[58] Field of Search ....... 73/425.4 R, 425.6, DIG. 9

[56] References Cited

UNITED STATES PATENTS

| | | | |
|---|---|---|---|
| 3,859,857 | 1/1975 | Falk | 73/425.4 R |
| 3,897,689 | 8/1975 | Boron | 73/425.4 R |
| 3,905,238 | 9/1975 | Falk | 73/425.6 |

*Primary Examiner*—Donald O. Woodiel
*Assistant Examiner*—Joseph W. Roskos
*Attorney, Agent, or Firm*—Fay & Sharpe

[57] ABSTRACT

The specification and drawings disclose an embodiment of an apparatus for taking samples from a flowing stream of molten metal. The apparatus comprises a container defining a sample mold cavity having a flat mold sample chamber and a pin sample chamber that are interconnected. The apparatus is so designed that a sample tube communicating with the mold cavity can be placed in the stream of molten metal to fill the cavity with a quantity of sample metal. The apparatus is externally ribbed to facilitate slidable housing in a suitable protective shield so that the sample tube may be selectively exposed for use in drawing a sample. The sample tube, mold sample chamber and pin sample chamber define a flow path which creates a turbulent flow of molten metal in the sample chambers thereby to equalize the carbon content of the sample metal in both the pin sample and mold sample chambers. The apparatus is preferably formed from molded sand and employs chill discs and vents to respectively aid in freezing the molten metal and to allow egress of air from the sample cavity.

17 Claims, 10 Drawing Figures

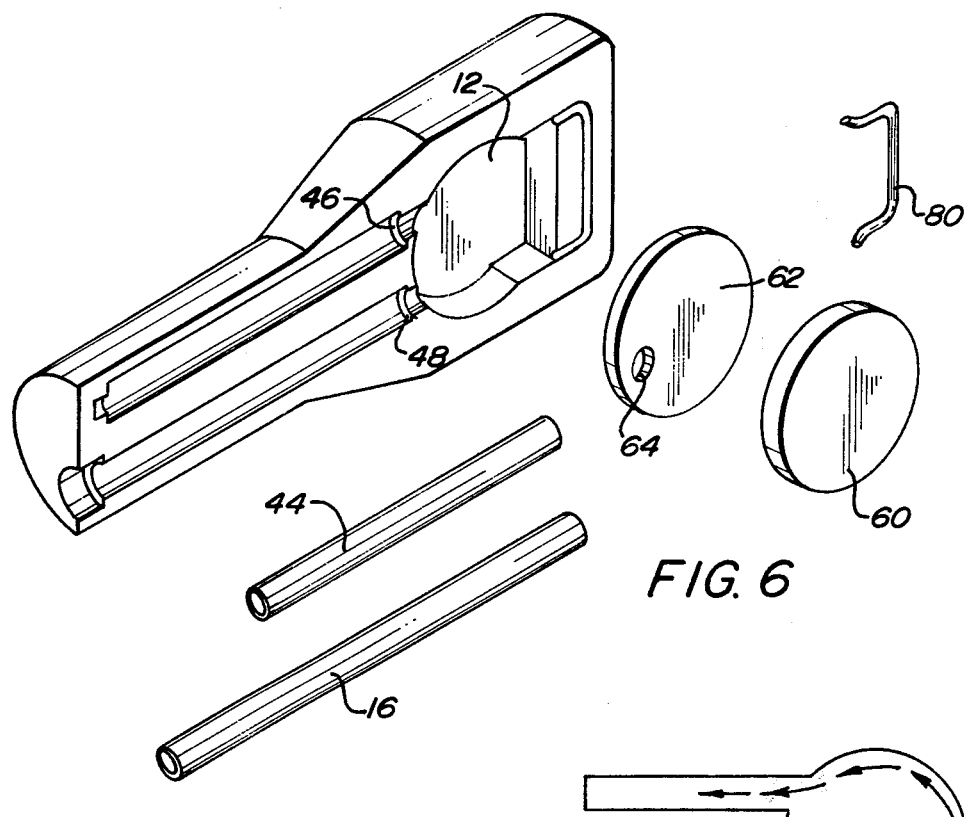
FIG. 6
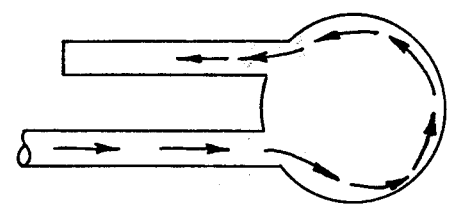
FIG. 7
FIG. 8 (PRIOR ART)
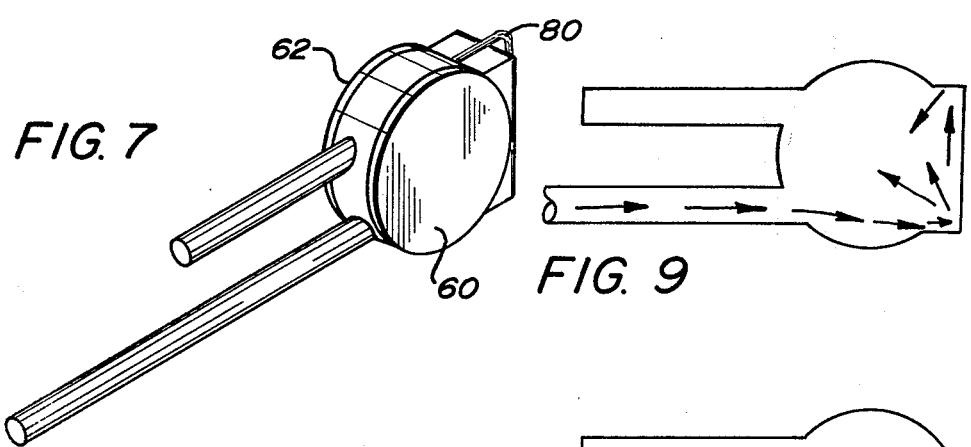
FIG. 9
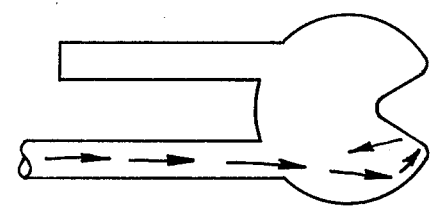
FIG. 10

SAMPLING APPARATUS

BACKGROUND OF THE INVENTION

1. Field of the Ivention

This invention relates to apparatus for obtaining a sample of molten metal from a flowing molten metal stream. Such apparatus is generally to be found in the U.S. Patent Office subclasses relating to measuring and testing, sampler and toller implements.

2. Description of the Prior Art

Apparatus in the prior art have generally been divided into two categories: Samplers that are designed to be immersed in molten material and apparatus that are designed to be inserted into a flowing stream of molten material. The problems encountered in designing sampling apparatus for use in each of the above two situations have generally been felt to be similar and for the most part they are. However, due to the fact that it is generally desirable to obtain a disc-like or flat sample along with a pintype sample the technology employed in designing an immersion-type sampler is not suitable in all respects for the design of a stream-type sampler.

In immersion-type samplers, mold chambers have been provided and, as described in U.S. Pat. No. 3,877,309, a venturi-type entry port, a pin sample tube and a flat sample mold cavity have also been employed. In the immersion sampler art it has been found to be desirable to reduce the resistance to flow of the molten metal entering the sample chambers thereby effecting smoother flow to form compact samples free of hollow areas.

In the stream sampler art, stream samplers such as those disclosed in U.S. Pat. No. 3,751,986 are formed having a substantially round transversely cross-sectioned disc-like cavity in association preferably with a pin-type sample appendage. An object of such prior art patent was the provision of a simplified and improved apparatus which provided adequate samples and which additionally provided means for housing the sampler in a versatile shipping container and which was further relatively inexpensive to manufacture and easy to use.

In the stream sampler art, however, problems have been encountered in equalizing the carbon content of the pin sample and disc-like sample. This problem is not so prevalent in the immersion sampler art. It can readily be appreciated though that substantial uniformity of carbon content in the sample is extremely important.

The stream and immersion sampler arts have also disclosed various attempts to provide sample containers made from molded sand. The use of such material has met with a degree of limited success, however, disadvantages are often encountered which have stemmed variously from the emission from the shell mold of objectionable substances associated with resin coated binders or the fact that the sand employed tended to provide a surface on the metal sample that was not smooth enough for testing purposes without preparation of the sample after its withdrawal from the mold cavity. A further difficulty encountered with core sand containers was that they were sometimes difficult to slide within their outer housings because of high friction between the sand and the housing.

It is also known in the art that in some applications it is desirable to vent the sample receiving cavity to the atmosphere. Problems also have been encountered in this regard since it has often been difficult to prevent the vent ports from undesirably filling with molten material thereby blocking escape of air from the inside of the chamber resulting in non-uniform samples. Various approaches have been taken to resolve this problem and the immersion sampler art and stream sampler art have approached solutions in somewhat different manners. This stems from the fact that the problem encountered in the two arts are at times somewhat divergent. Insofar as prior art venting methods are concerned it has also been found that the addition of an air permeable quantity of material in the vent port eliminated run out of material from the inside of the cavity. Of course, this adds to the cost of the unit and necessitates an additional manufacturing step.

SUMMARY OF THE INVENTION

The subject invention provides an improved construction for a device for taking samples from a stream of molten metal. Sampling devices formed in accordance with the invention are more efficient and provide a better sample of metal than prior devices. Further, the subject invention overcomes problems previously encountered in equalizing the carbon content of the pin sample and the flat sample which are produced in a single mold container. Additionally, improvements to the outside configuration of a core sand container have been made to facilitate slidable cooperation with an outer shipping and handling housing. Improvements have also been made in the venting system and in chilling the metal sample that is being obtained.

In particular, the invention contemplates an assembly which includes a mold container having a sample receiving tube joined thereto. The mold container and sample tube are positioned in a tubular open-ended housing and the mold is provided with longitudinally extending ribs to aid in relative sliding movement between the housing and the mold between at least two positions including a first position wherein the sample tube is enclosed and protected by the housing and a second position wherein the tube extends from the housing for taking a sample. The mold is internally conformed to provide a flat or disc-like sample and a pin-type sample which are substantially equal in carbon content. Provision is also made for the attachment to the samples of a tagging loop for indentification purposes.

More specific aspects of the invention contemplate that preferably, but not necessarily, the mold container will be made from core sand and chill discs will be provided inside the mold cavity defined by the container, one of which discs will become welded to the sample and the other of which will be removable from the sample when the frangible container is broken preparatory to testing the sample metal.

Preferably, but also not necessarily, the housing cylinder is mounted on a handle when the sampling apparatus is used for sample taking and the sample tube, which is preferably secured to the core sand container, may be selectively exposed from the housing for sample taking.

Provision has also been made to guard against the vent aperture, which communicates with the mold cavity, from becoming plugged during the sample taking procedure.

Accordingly, the primary object of the invention is the provision of an improved apparatus for taking samples from streams of molten metal.

Another object is the provision of an apparatus of the type described wherein pin and disc-like samples can be obtained which are substantially equal in carbon content. Another object is the provision of an outer tubular housing which serves both as a shipping unit and also provides a means for mounting the assembly for taking samples and in which a sand mold is suitably ribbed to facilitate relative movement of the outer housing and the mold cavity container. Yet a further object is the provision of a means for chilling the sample by use of chill discs, one of which will become attached to the sample and one of which will be readily removable therefrom.

Yet another object of the invention is to provide a sample that can be analyzed in a laboratory without avoidable sample preparation.

The above and other objects and advantages will become more readily apparent when the following description is read in conjunction with the accompanying drawings wherein.

Figure 3:
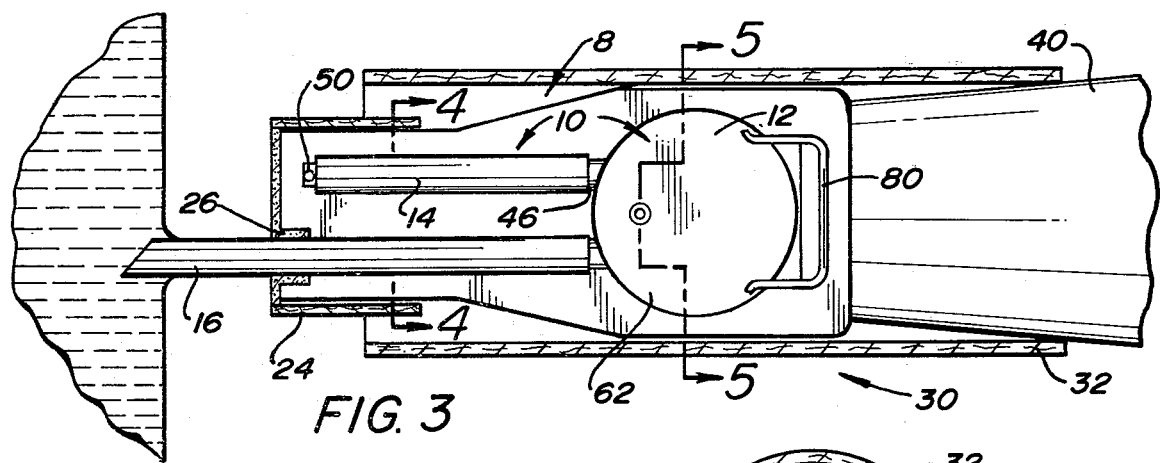
FIG. 3 is a cross-sectional view taken along line 3—3 of FIG. 2.
Figure 4:
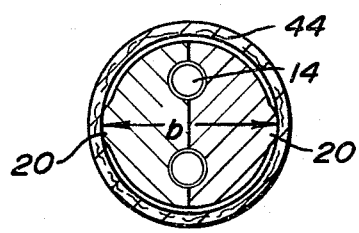
Figure 5:
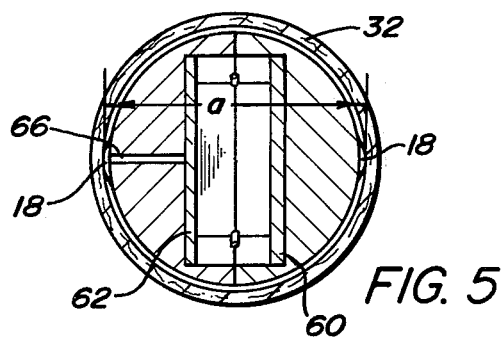

FIGS. 4 and 5 are cross-sectional views taken along lines 4—4 and 5—5, respectively, of FIG. 3;

FIG. 6 is an exploded pictorial view of a portion of the sample container;

FIG. 7 is a pictorial view of a solidified sample after removal from the sampling apparatus;

FIG. 8 is a schematic representation of metal flow in prior art devices;

FIG. 9 is a schematic representation of metal flow in one embodiment of the sampling apparatus described herein; and FIG. 10 is a schematic representation of metal flow in another embodiment of the sampling apparatus disclosed herein.

Figure 1:
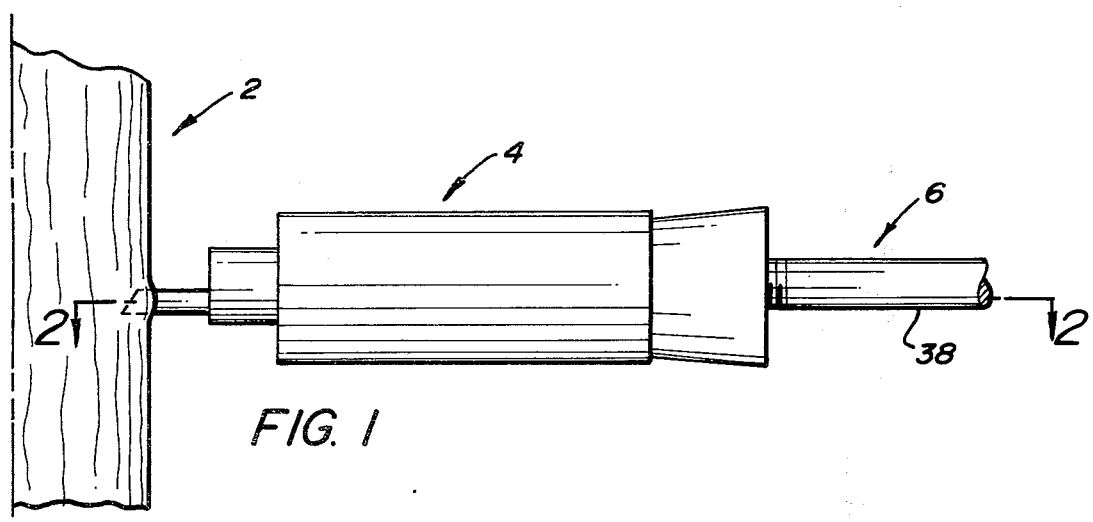
FIG. 1 is an elevational view showing a sampling apparatus formed in accordance with the invention and being used for obtaining a sample from a stream of molten metal.

Referring more particularly to the drawings wherein the showings are for the purpose of illustrating preferred embodiments of the invention only, and not for the purpose of limiting same, FIG. 1 shows a stream of molten metal 2 which can, for example, be coming from a pouring ladle or the like. A sampling device 4, formed in accordance with the invention is illustrated as being mounted at the end of a long handle or lance member 6 and is positioned for taking a sample of molten metal from stream 2 for subsequent analysis or testing.

Figure 2:
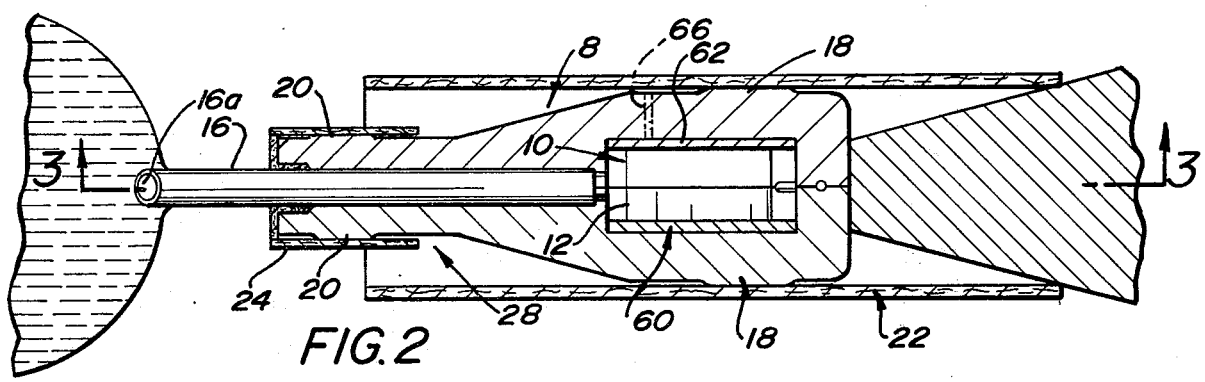
FIG. 2 is an enlarged, cross-sectional view taken along line 2—2 of FIG. 1.

FIGS. 2 and 3 best illustrate the details of the preferred embodiment of the sampling assembly 4.

In FIGS. 2 and 3 the sampling apparatus is shown in sampling position.

In general, the sampling apparatus is shown including a container 8 which defines a mold cavity 10 which comprises both a mold chamber 12 and a pin chamber 14. Joining the container and partially enclosed therein is a sample tube 16 which communicates with the mold cavity and along with the mold and pin chambers defines a flow path for molten metal. The sample tube 16 is formed from a material capable of withstanding the high temperature and thermal shocks experienced in taking a sample from the molten metal stream.

The container 8 comprises ribs 18 and 20 which extend longitudinally of the container. The ribs 18 are designed to slidably contact outer housing 22 and the ribs 20 are designed to engage sleeve 24.

The interior of the container is hollowed out as shown so as to readily define the mold chamber, pin chamber, and the passage for receipt of sample tube 16.

In the embodiment under consideration, the sample tube 16 is joined to the sample mold by a refractory cement 26. A thin-walled sleeve 24 is positioned about the neck portion 28 of the mold container. The tube or sleeve 24 may serve, if necessary, to confine the refractory cement until it hardens. If the container is made in sections, it may also serve to hold the container together.

The sample tube and sample mold assembly are mounted in a housing 30 which housing comprises an elongated tubular member 32. As is shown, the tubular member is cylindrical in shape and open at both ends. It is preferably made of heavy paperboard. The inner diameter of the cylinder 32 is preferably approximately equal to the diagonal dimension, $a$, between the outside of ribbed portions 18. This is best seen in FIG. 5. The inside diameter of sleeve portion 24, on the other hand, is preferably about equal to the diameter $b$ shown in FIG. 4. This dimension is approximately the outside diameter defined by ribbed portions 20. These features allow both the neck sleeve portion and the outside housing to easily slidably engage the core and mold container. The mold container slides within outer housing 30 and the entire assembly is oriented and used in a manner similar to that described in U.S. Pat. No. 3,751,986.

The housing 30 serves multifunctional purposes. It encloses the core sand container and sample tube during shipment when the container and tube are withdrawn into the housing in a configuration not shown in the drawings. Additionally, the core sand container is slidable to expose the sample tube in operating position when it is desired to put the unit into use for taking samples of molten metal. The ribbed features about the body of the container in the area of its greatest diameter facilitate relative sliding movement of the housing and the core sand container.

Lance member 38 threadedly connects to a conically shaped adapter 40, and together they are employed to support the sampling apparatus during use thereof.

Insofar as the molten metal sample itself is concerned, it has been found desirable to provide an interconnected disc-like and pin-type sample. In order that the outside walls of the pin sample be fairly smooth for certain testing procedures, such as sulfur analysis, it has been found to be desirable to insert a thermal shock impervious sleeve or tube 44 into the pin sample cavity. The tube can be loosely contained within the cavity. It is preferable though that the sample tube abut a shoulder portion 46 which facilitates positioning the tube. It will be appreciated that the pin sample tube can be formed from any suitable thermal shock resistant material such as quartz or Pyrex glass. This is true also of the sample inlet tube. It will also be appreciated that the sample inlet tube, similar to the positioning of the pin tube, also abuts against a shoulder portion (48) but, as previously mentioned, the sample inlet tube is cemented in place.

Referring now to the mold chamber 12 it will be seen that it is uniquely and irregularly configured. It has been found that in prior art devices, such as that schematically depicted in FIG. 8, metal flow into the sample tube tended to take a direct route from the sample tube into the pin sample chamber. This has been found to be objectionable. Since, necessarily, the sample tube which is illustrated at 16 in the preferred embodiment described herein contacts a stream of molten metal at its outside edge first it tends to contact metal having a lower carbon content than the metal found in the interior of the stream.

It has been theorized that the metal on the outside of the stream exhibits this characteristic because the carbon in the metal on the outside of the stream is in contact more directly with the atmosphere and thus tends to oxidize more readily than the metal on the inside of the stream thus resulting in a lower carbon content. As a result of this oxidation, the pin portion of the sample that was eventually obtained was objectionably lower in carbon content than that of the disc or flat-like sample which filled after the lance has been inserted more to the interior of the stream of flowing molten metal. In order to avoid this objectionable feature the applicant has designed the flow path and mold chamber portion of the core sand container so as to substantially equalize the carbon content of the disc sample and the pin sample by creating a turbulent flow of metal within the mold cavity. This turbulent flow of metal can be achieved in a number of ways employing different designs, such as baffles or the like, two of which designs are schematically shown in FIGS. 9 and 10.

Referring again now to FIGS. 2 and 3 it will be seen that the open ends 16a of the sample tube contacts a stream of molten metal during use of the apparatus and sample taking. The molten metal flows through the sample tube and into the mold cavity. In the mold chamber 12, a turbulent flow is created and the molten metal initially entering the sample tube is limited from directly entering the pin sample tube. It should be understood that air within the mold cavity is driven out through vent 50 which communicates with the pin sample chamber. It will be seen that the vent provided in the pin sample chamber extends radially therefrom and as a consequence will not readily fill or become clogged with molten metal when the apparatus is inserted into a stream of molten metal.

Due to the ribbing of the container in the neck portion, sleeve 24 is held a slight distance from the opening so that venting can be accomplished easily.

Referring now with more particularity to the mold chamber it will be seen that two chill discs 60 and 62 are provided. These discs aid in rapidly freezing the molten metal. Additionally, it will be seen that disc 62 is apertured at 64 and that provision has been made for venting the mold cavity in the area of contact of disc 62 with the interior of the mold chamber at vent port 66. It will also be readily appreciated that venting is facilitated because of the provision of ribs 18 which hold housing 30 at a distance from the outside opening of the port.

It can be seen from the drawings that the chill discs that are provided are of different thicknesses and in the preferred embodiment of the invention the thinner chill disc having the vent aperture is preferably made of steel. This combination of a thin disc and a steel composition enables the disc to become welded to a molten steel sample. The composition of the disc may vary, of course, in order to adapt it to more readily weld to the molten material being sampled.

The disc 62 has a smooth outer surface and easily conducts electricity for testing purposes after the sample has been withdrawn from the mold which, as previously mentioned, is of a frangible character so that it may be easily broken after the sample has frozen inside. The bottom disc 60, when employed in molten steel testing, is preferably made of a powdered iron material and is of thicker construction so as to inhibit welding of said disc to the disc-like or flat sample produced in the mold cavity. It is thus readily removable from the sample and will create a smooth surface on the sample for good electrical attachment of electrodes or the like for testing purposes.

Provision has also been made for the attachment of a tagging loop 80 to the sample. The tagging loop can be formed from a small section of wire and can be positioned in the mold in the manner shown. The ends of the tagging loop 80 extend into the mold cavity. Thus, after a sample is taken and solidified, the loop is permanently attached as shown in FIG. 7. This allows identification tags to be readily attached to the sample.

FIG. 7 illustrates generally the configuration of a sample taken in accordance with the preferred embodiment of the invention after it has been removed from the mold container. It will be appreciated that in the view shown chill disc 60 has not been removed from the sample but this, as previously explained, is readily accomplished due to its size and composition.

In the embodiment shown the mold has been described as being made from core sand. It is also anticipated that other suitable materials can readily be substituted for core sand such as a ceramic composition or even glass. It will further be appreciated that the sampler as described is made of two substantially identical halves which join in mating relationship and are held together by the external housing 30 and sleeve 24. It should be understood that the apparatus can be made of unitary construction since the material contemplated for use in forming the container will disintegrate readily for removal of the sample. It will be appreciated also that with the provision of the vent ports that even when the mold is made of two halves which are substantially mirror images of each other that "finning" is substantially eliminated. It will also be appreciated that the vent in the pin sample and flat sample chambers substantially eliminates any shrinkage problem that has previously been encountered. It should also be understood that various other configurations or baffle-like structures could be employed in the flow path to substantially equalize carbon content by forcing the metal being sampled to work itself into the pin sample area by breaking up the flow of molten metal being sampled.

The invention has been described in great detail sufficient to enable one of ordinary skill in the art to make and use the same. Obviously, modifications and alterations in the preferred embodiment will occur to others upon a reading and understanding of the specification. All such alterations are to be considered as part of the invention insofar as they come within the scope of the appended claims.

What is claimed is:

1. Apparatus for taking a sample from a flowing stream of molten metal comprising:
    container means defining a mold cavity having a mold chamber and a pin chamber communicating with each other for receiving a sample quantity of said molten metal and forming a mold chamber sample and a pin sample;

a sample tube communicating with said mold chamber and having an open end adapted to be placed in said stream of molten metal for supplying said metal to said tube and chambers;

said mold chamber, pin chamber and sample tube defining a flow path;

means in the flow path for substantially equalizing the carbon content of the pin sample and the mold chamber sample.

2. The apparatus of claim 1 wherein said container means is longitudinally externally ribbed.

3. The apparatus of claim 2 further comprising an open ended tubular housing slidably enclosing said container means.

4. The apparatus of claim 1 wherein said container means is molded from sand.

5. The apparatus of claim 1 wherein vent means is provided communicating with said mold cavity.

6. The apparatus of claim 1 wherein metal chilling means is provided in the mold chamber.

7. The apparatus of claim 1 wherein the pin chamber is cylindrical and wherein vent means is provided communicating with said pin chamber and extending substantially radially therefrom.

8. The apparatus of claim 6 wherein said metal chilling means comprises a chill disc and wherein said disc is weldable to the sample formed in the mold chamber.

9. The apparatus of claim 6 wherein said metal chilling means comprises a chill disc being readily detachable from the sample formed in the mold chamber.

10. The apparatus of claim 6 wherein said metal chilling means is a chill disc having vent means therein.

11. The apparatus of claim 1 wherein said means for substantially equalizing carbon content comprises a baffle.

12. Apparatus for taking a sample from a flowing stream of molten metal comprising:

container means defining a mold cavity having a mold chamber and a pin chamber communicating with each other for receiving a sample quantity of said molten metal;

a sample tube communicating with said mold chamber and having an open end adapted to be placed in said stream of molten metal for supplying said metal to said tube and chambers;

said mold chamber, pin chamber and sample tube defining a flow path; and, means in the flow path for causing molten metal entering said path to flow turbulently.

13. The apparatus of claim 12 wherein said container means is molded from sand:

14. The apparatus of claim 12 wherein vent means is provided communicating with said mold cavity.

15. The apparatus of claim 12 wherein metal chilling means is provided in the mold chamber.

16. The apparatus of claim 12 wherein the pin chamber is cylindrical and wherein vent means is provided communicating with said pin chamber and extending substantially radially therefrom.

17. The apparatus of claim 12 wherein vent means is provided communicating with said mold cavity, said vent means being located so that substantially no metal will flow into it when the open end of the sample tube is placed in the stream of molten metal.

* * * * *